United States Patent
Schoen et al.

(10) Patent No.: US 9,594,241 B2
(45) Date of Patent: Mar. 14, 2017

(54) TRANSMITTED-LIGHT MICROSCOPE AND METHOD FOR TRANSMITTED-LIGHT MICROSCOPY

(71) Applicant: Carl Zeiss Microscopy GmbH, Jena (DE)

(72) Inventors: Peter Schoen, Goettingen (DE); Ralf Steinmeyer, Hannover (DE); Maik Sommer, Seeburg/Bernhausen (DE); Klaus Becker, Breitenworbis (DE)

(73) Assignee: Carl Zeiss Microscopy GmbH, Jena (DE)

( * ) Notice: Subject to any disclaimer, the term of this patent is extended or adjusted under 35 U.S.C. 154(b) by 0 days.

(21) Appl. No.: 14/795,530

(22) Filed: Jul. 9, 2015

(65) Prior Publication Data
US 2016/0041377 A1    Feb. 11, 2016

(30) Foreign Application Priority Data

Jul. 9, 2014   (DE) .................. 10 2014 213 348

(51) Int. Cl.
*G02B 21/08*    (2006.01)
*G01N 21/03*    (2006.01)
(Continued)

(52) U.S. Cl.
CPC ....... *G02B 21/086* (2013.01); *G01N 21/0303* (2013.01); *G01N 21/11* (2013.01); *G02B 21/26* (2013.01); *G01N 2021/0325* (2013.01)

(58) Field of Classification Search
CPC ...... G02B 21/086; G02B 21/00; G02B 21/06; G02B 21/24; G02B 21/26; G02B 21/32;
(Continued)

(56) References Cited

U.S. PATENT DOCUMENTS 6,052,224 A * 4/2000 Richardson ............. B01L 3/508
                                                        359/398
6,411,433 B1 * 6/2002 Miyoshi ................. G02B 21/34
                                                        359/368
(Continued)

FOREIGN PATENT DOCUMENTS

DE            19916748 A1    10/2000
DE       102005033927 A1     3/2003
(Continued)

OTHER PUBLICATIONS

Cell Cultivator: http://www.ipm.fraunhofer.de/en/solutions-markets/environment-health/cell-analysis-and-culture/cellcultivator/cellcultivator.html; Fraunhofer Institute for Physical Measurement Techniques IPM, Freidburg, DE; No date provided (2 pgs).

*Primary Examiner* — Frank Font
(74) *Attorney, Agent, or Firm* — Patterson Thuente Pedersen P.A.

(57) ABSTRACT

A transmitted-light microscope for imaging well-shaped, liquid-containing sample vessels, wherein the transmitted-light microscope has an illumination beam path for illuminating the sample vessel with an illumination beam bundle, from above, along an optical axis, wherein the illumination beam path has an illuminating element aligned to the optical axis, which element irradiates the illumination beam bundle onto the sample vessel, an imaging beam path for imaging the sample vessel from below along the optical axis and a pipette access channel for introducing a reagent into the sample vessel, wherein the illuminating element is annular and has an opening on the optical axis through which opening runs the pipette access channel.

9 Claims, 6 Drawing Sheets

(51) Int. Cl.
*G01N 21/11* (2006.01)
*G02B 21/26* (2006.01)

(58) Field of Classification Search
CPC .... G02B 21/34; G01N 21/0303; G01N 21/11;
G01N 2021/0325
USPC .................................................. 359/387, 398
See application file for complete search history.

(56) References Cited

U.S. PATENT DOCUMENTS

| | | | |
|---|---|---|---|
| 2003/0143637 A1* | 7/2003 | Selvan | G01N 21/07 506/9 |
| 2005/0012990 A1* | 1/2005 | Otaki | G01N 35/109 359/368 |
| 2005/0196325 A1 | 9/2005 | Bathe et al. | |
| 2012/0034596 A1 | 2/2012 | Seidl et al. | |
| 2013/0164828 A1 | 6/2013 | Dholakia et al. | |
| 2014/0118820 A1 | 5/2014 | Kanecki et al. | |
| 2014/0160560 A1* | 6/2014 | Tomioka | G02B 21/06 359/388 |
| 2014/0273188 A1* | 9/2014 | Mohan | G01N 21/0303 435/287.2 |
| 2014/0329300 A1* | 11/2014 | Lundt | G01N 1/31 435/287.2 |

FOREIGN PATENT DOCUMENTS

| | | |
|---|---|---|
| DE | 10142788 A1 | 6/2007 |
| JP | 2004-271471 A | 9/2004 |

* cited by examiner

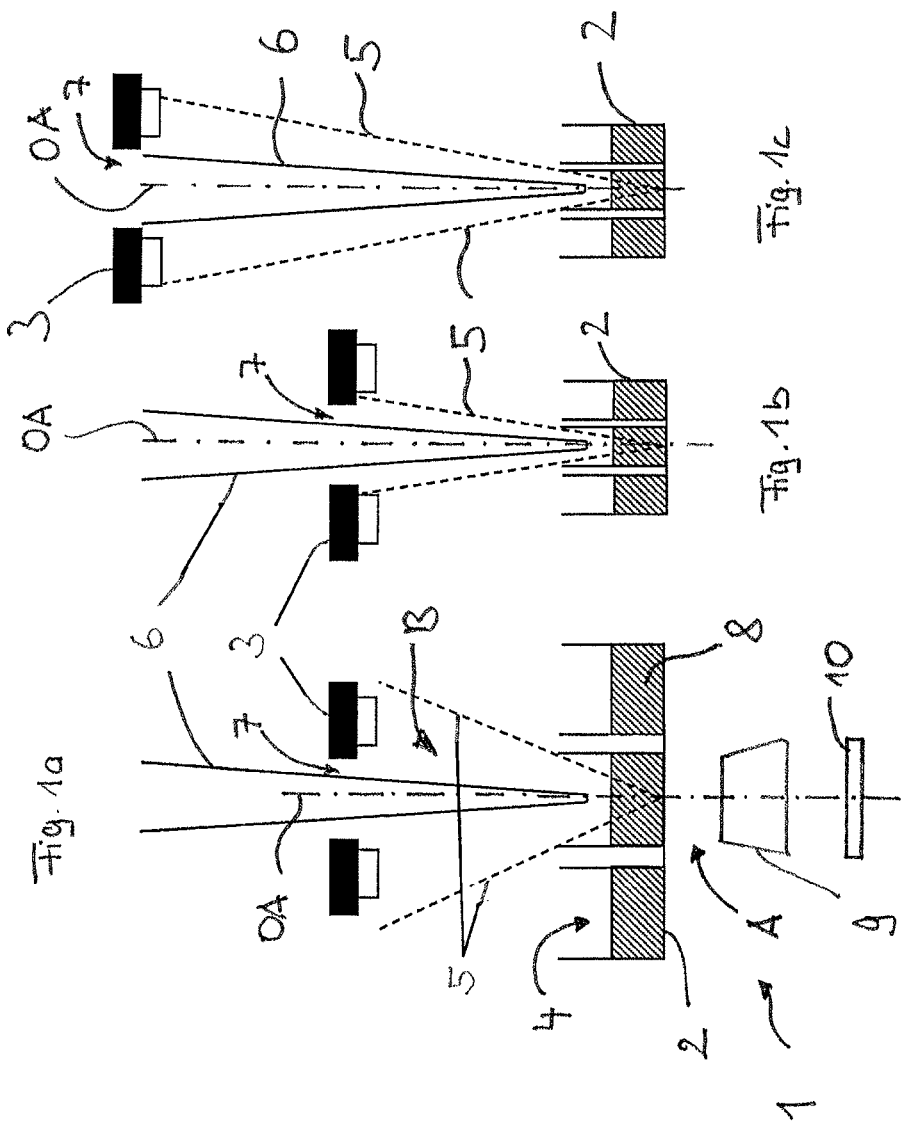

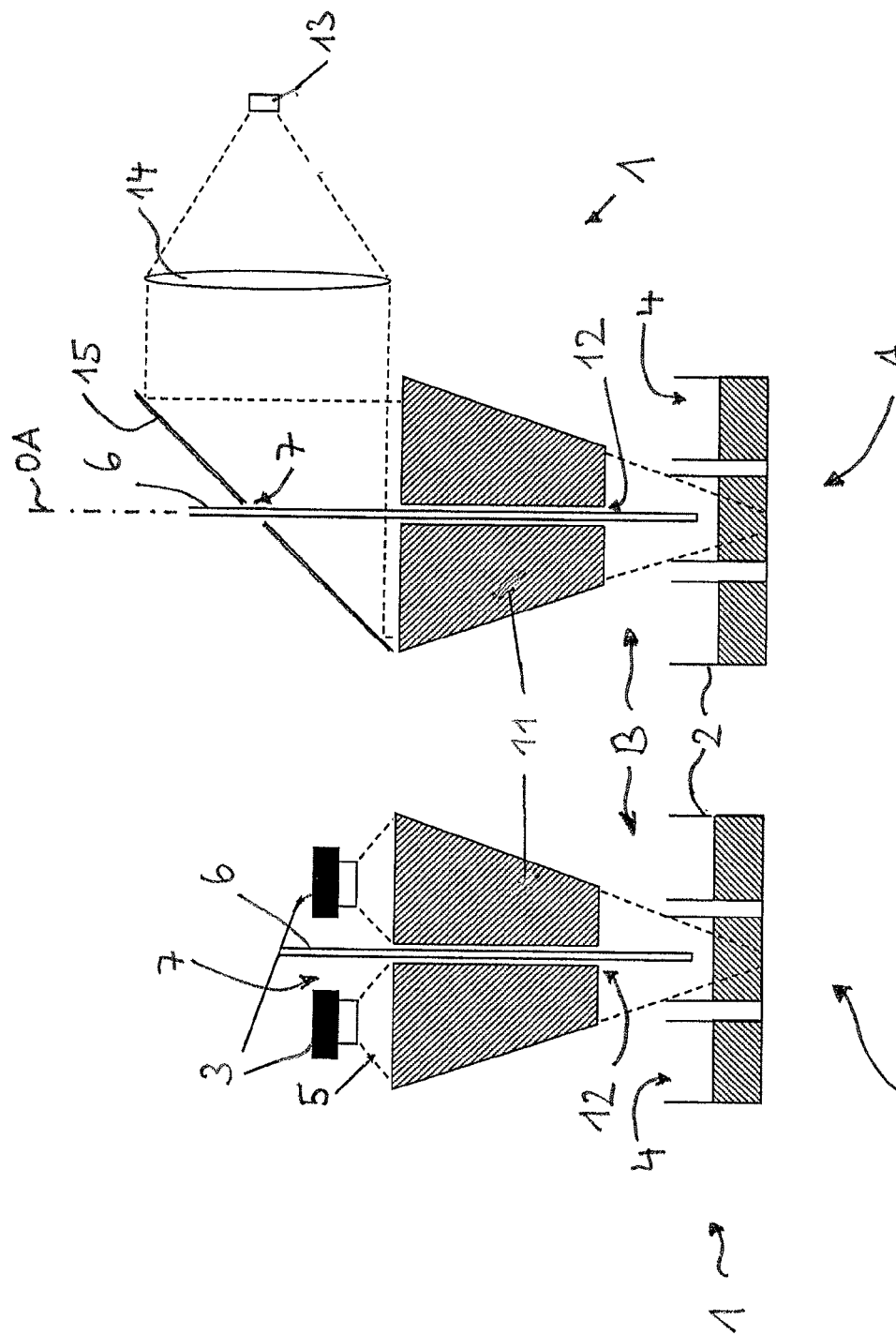

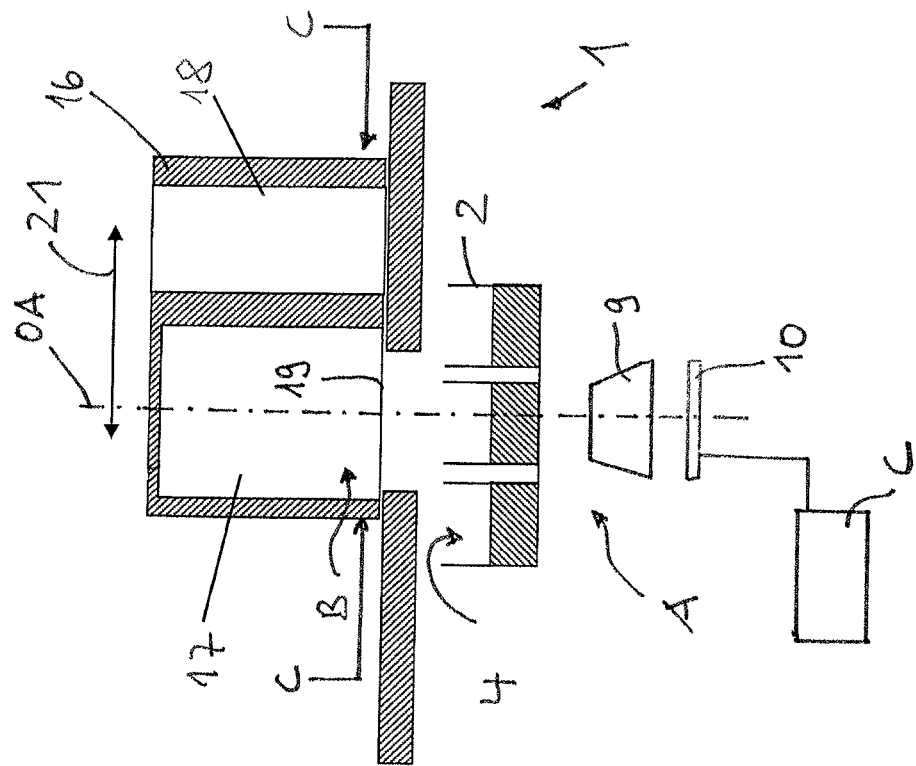
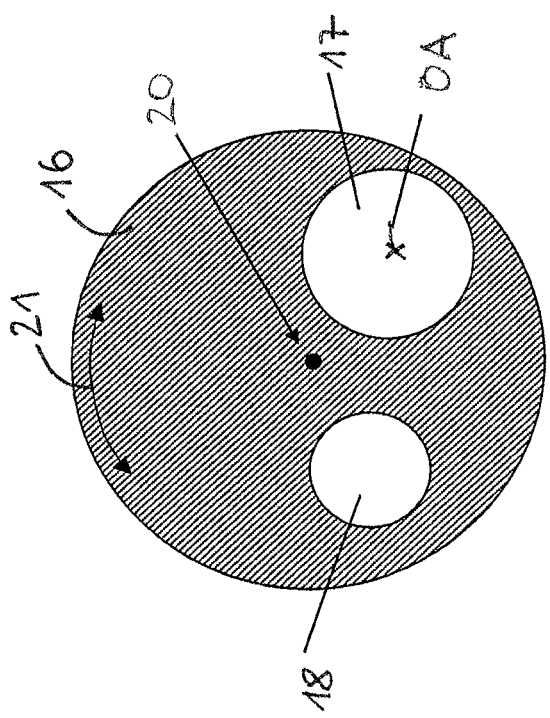

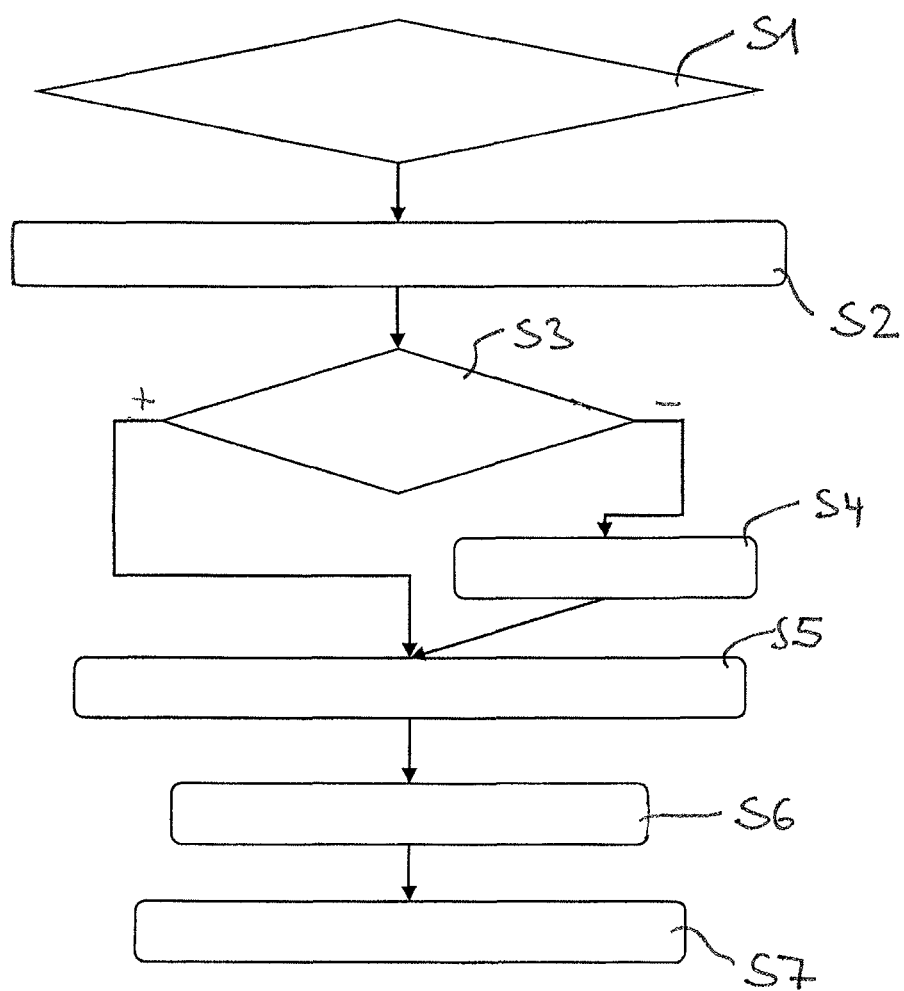

TRANSMITTED-LIGHT MICROSCOPE AND METHOD FOR TRANSMITTED-LIGHT MICROSCOPY

RELATED APPLICATION

The present application claims priority to German Application No. 102014213348.3, filed Jul. 9, 2014, said application being hereby fully incorporated herein in its entirety by reference.

FIELD OF THE INVENTION

The invention relates to a transmitted-light microscope for imaging well-shaped, liquid-containing sample vessels, wherein the transmitted-light microscope has: an illumination beam path for illuminating the sample vessel with an illumination beam bundle, from above, along an optical axis, an imaging beam path for imaging the sample vessel, from below, along the optical axis, and a pipette access channel for introducing a reagent into the sample vessel.

The invention also relates to a method for transmitted-light microscopy of well-shaped, liquid-containing sample vessels, wherein the sample vessel is illuminated with an illumination beam bundle, from above, along an optical axis, the sample vessel is imaged, from below, along the optical axis and a reagent is introduced into the sample vessel via a pipette access channel.

BACKGROUND OF THE INVENTION

Microscopy of live cells plays an important role in biomedical sciences. These are usually cultivated in vessels such as microtiter plates or Petri dishes. The cells are located on the bottom of the vessel and are surrounded by a culture medium. They are subjected to microscopy with an inverted microscope; in this microscope the objective is located beneath the bottom of the sample vessel. The sample can be illuminated via incident light or transmitted light. For transmitted-light images a light is attached above the sample vessel. However, as biological cells contain only few absorptive constituents, bright-field transmitted-light images are typically contrasted only very weakly. With the help of various transmitted-light contrasting methods, such as phase contrast, DIC, inter alia, the small difference in refractive index of the individual cell constituents from one another and from the surrounding medium can be converted into an intensity difference which then provides a contrasted transmitted-light image, but from this frequently only little can be said about the functions or distributions of specific substances within the cell. Fluorescence microscopy solves this problem by specific substances (fluorophores) already available to the cells or which have been introduced into same being excited with the help of incident-light illumination, which fluorophores then in turn emit a signal which is captured by the objective and is transmitted to the camera or the oculars. Because, however, only those structures can be seen, the fluorophores of which are excited, information about the size and shape of the individual cells can become lost. Therefore, incident and transmitted light are frequently combined as they provide complementary information.

Living cells are not static objects but are permanently changing as they are alive. In particular, they can act as the subject of studies into the effects of environmental influences on living organisms. These influences also include the material composition of the nutrient medium. If this is changed, the cell reacts to it. The reaction times can lie in the range of minutes and hours, but also seconds. It may thus be of decisive importance that observation takes place immediately after or indeed during a change to the cell environment. The change to the environment is usually achieved by the pipetting the substance, the effect of which is to be investigated, into the nutrient solution. As the sample vessels are open at the top, the reagents are also introduced from the top. Thus a spatial conflict with the transmitted-light illumination is intentional.

SUMMARY OF THE INVENTION

There is a number of possibilities for solving this conflict, each of which has its own specific advantages and disadvantages. US 2012/0034596 describes a device in which the sample vessel can be transported in a holder from one area in which reagents can be introduced into another area where the optical elements for microscopy are located. Reagent is then introduced directly from above at any point of the sample vessel. The disadvantage of this method is that the sample needs to be moved a great distance between being introduced and being observed, and reactions of the cells which take place immediately after introduction cannot be detected. Moreover, generally, comparative image are required before the introduction of reagents, i.e. a position on the sample suitable for microscopy must firstly be found, then the sample vessel travels to the position where introduction takes place, and then back again. This leads to several movements of the samples which also means stress for the cells and can lead to reactions which have nothing to do with the actual introduction of reagents.

In order to achieve an introduction at the observation position, the pipette may also be attached inclined from the side. This is possible in sample vessels with large openings such as e.g. Petri dishes, but, in microtiter plates with e.g. 96 or 384 wells, as are frequently used, leads to great difficulties as the pipette cannot be positioned at a sufficient angle to guarantee that it is immersed into the nutrient solution. It is also indeed possible to pipette above the medium, but this carries the risk that a drop of the liquid to be pipetted remains on the tip of the pipette. This leads to a difference between the desired and the actual concentration of the pipetted liquid in the nutrient medium. In particular, with small volumes to be pipetted, the relative error can take on very high values or the quantity to be pipetted does not leave the tip of the pipette at all which can lead to incorrect test results.

This can be countered by using curved pipette tips, the latter end of which can be immersed perpendicularly into the liquid. Even in this case, there may be only very little room for manoeuvre between the sample vessel and the transmitted-light illumination placed above same. Thus it can occur that firstly the transmitted-light illumination or parts thereof (e.g. a condenser) need to be raised before the introduction, before the tip of the pipette can be positioned in order then to lower the illumination again. In particular when using microtiter plates with many wells, the possibility of automation increases in importance. It can also be achieved in the case just described, but requires a number of movements which are carried out sequentially: Raising the illumination, laterally inserting the tip of the pipette, lowering the tip of the pipette, lowering the illumination. In fact, the simultaneous introduction and transmitted-light observation is now possible, but the tip standing to the side in the image impairs the quality of the transmitted-light images. Consequently, it may be necessary to remove the pipette again from the illumination beam path before taking the picture.

A further difficulty in curved tips of pipettes consists of a slight rotation already leading to the bent end piece no longer pointing perpendicularly downwards, but remaining inclined. In small wells, such as e.g. in microtiter plates with 384 wells, collisions with the edge of the well then become very likely. If it is desired to avoid needing to use bent pipettes, the illumination objective can be raised so far that a straight pipette tip can be placed between sample and illumination and bending occurring only thereafter. Such a solution was achieved at the Fraunhofer-Institut für Physikalische Messtechnik in the CellCultivator. However, transmitted-light illumination and introduction of reagents are only sequentially possible and the height of lift of the objective is substantial. Moreover, various movements still need to be carried out, for each of which an individual drive system is needed: Lifting the illumination, horizontal positioning of the introducing device, lowering the tip of the pipette.

The object of the invention is to provide a transmitted-light microscope and a method for transmitted-light microscopy, with the result that a reagent can be introduced into a sample vessel without the described disadvantages.

The object is achieved with a transmitted-light microscope for imaging well-shaped, liquid-containing sample vessels, wherein the transmitted-light microscope comprises:

an illumination beam path for illuminating the sample vessel with an illumination beam bundle, from above, along an optical axis, an imaging beam path for imaging the sample vessel, from below, along the optical axis and a pipette access channel for introducing a reagent into the sample vessel, wherein the transmitted-light microscope also has a block which has a passage for the illumination beam bundle and a through channel, through which passage runs the pipette access channel, wherein the through channel and the passage lie adjacent to one another in a plane perpendicular to the optical axis, a guide device for the block, which device provides a first position for the block in which the through channel is aligned to the optical axis and a second position in which the passage is aligned to the optical axis and provides a path between the first position and the second position, wherein the path follows a single movement, and a drive mechanism which moves the block between the first position and the second position by the single movement.

The object is ultimately also achieved with a method for transmitted-light microscopy of well-shaped, liquid-containing sample vessels, wherein the sample vessel is illuminated with an illumination beam bundle, from above, along an optical axis, the sample vessel is imaged, from below, along the optical axis and a reagent is introduced into the sample vessel via a pipette access channel, wherein a block is used which has a passage for the illumination beam bundle and a through channel, through which passage runs the pipette access channel, wherein the through channel and the passage lie adjacent to one another in a plane perpendicular to the optical axis, the block is moved by a single movement between a first position in which the through channel is aligned to the optical axis and a second position in which the passage is aligned to the optical axis.

This object is also achieved with a transmitted-light microscope for imaging well-shaped, liquid-containing sample vessels, wherein the transmitted-light microscope comprises:

an illumination beam path for illuminating the sample vessel with an illumination beam bundle, from above, along an optical axis, wherein the illumination beam path has an illuminating element aligned to the optical axis, which element irradiates the illumination beam bundle onto the sample vessel, an imaging beam path for imaging the sample vessel, from below, along the optical axis and a pipette access channel for introducing a reagent into the sample vessel, wherein the illuminating element is annular and has an opening on the optical axis, through which opening runs the pipette access channel.

The object is also achieved with a method for transmitted-light microscopy of well-shaped, liquid-containing sample vessels, wherein:

the sample vessel is illuminated with an illumination beam bundle, from above, along an optical axis, wherein an illuminating element aligned to the optical axis is used, which element irradiates the illumination beam bundle onto the sample vessel, the sample vessel is imaged, from below, along the optical axis and a reagent is introduced into the sample vessel via a pipette access channel, wherein an annular illuminating element is used which has an opening on the optical axis through which opening runs the pipette access channel.

In the first variant, the transmitted-light illumination and introduction of reagents are carried out sequentially, wherein the transmitted-light illumination and the introduction channel are switched by a single movement on the optical axis.

This can happen e.g. by rotating the block, which can be rotated in at least two positions, wherein in one position the transmitted-light illumination is located over the sample, and in another position a free channel is available for reagents to be introduced. In this pipetting process a pipette can then be introduced either manually or via a robot.

The pipetting device can optionally already be held available in the apparatus. In this connection it does not always matter how the transmitted-light illumination is designed: whether as a point source with or without an additional objective, or whether as an area light with or without an additional objective. However, it is advantageous if large matter far away from the axis of rotation are avoided. Therefore, a transmitted-light illumination without a deflecting mirror is to be preferred. Such an illumination can break down for longer than pipettes customary in the trade. This leads to conflicts if both the transmitted-light illumination and also access to the pipette are to have a common housing, as in this case the tip of the pipette no longer reaches the sample.

The two positions (transmitted-light illumination, pipette access) can be set by lateral movement of the block. Also in this case only one movement is needed to switch from transmitted light to pipetting. Simultaneously, in this case, the illumination beam path can be bent without problems by means of a deflecting mirror, with the result that a common housing can be provided for the transmitted light and the introduction channel.

When introducing reagents, it is important that this takes place at the correct height. If pipetting takes place from too high up, the tip of the pipette is not immersed in the nutrient liquid and partial quantities or the whole of the substance to be pipetted can remain on the tip. If pipetting takes place from too low down, the tip of the pipette may catch on the floor of the sample vessel and destroy the sample at this location. It requires a great degree of skill to pipette into the free space and hold the pipette still. Therefore, a stop, against which a part of the pipette or the tip of the pipette can be placed, is advantageous. On this point, the tip of the pipette has for example a collar which is already present in any case. The height of this stop above the pipetting position can be set either fixed or chosen to be variable, in order to adapt the insertion channel to the pipette or tip of the pipette used, as well as to the height of the sample plane. This height can vary by several millimeters. Microtiter plates e.g. can have bottoms made of a thin film or bottoms which are made of polystyrene which is 1 mm thick. Moreover, they do not usually lie on this bottom, but have a circumferentially offset edge which creates an air space of several millimeters below the individual wells. However, this value varies from manufacturer to manufacturer and is also standardised only by the establishment of a minimum value. Also, this standard is frequently not reached in the microplates used for microscopy in order to make possible the use of objectives with high numerical aperture and therefore a consequentially large diameter. Accordingly, the sample plane is located at different heights relative to the sample holder and thus also to the pipette access.

A possible method for reacting to this variability is as follows: The height of the pipette stop or the whole feed unit is designed to be adjustable. Before the introduction begins, a program requests the tip of the pipette used and searches for the corresponding length from the end of the collar to the tip from a list. Then, the objective is moved along the optical axis such that the sample lies in the focal plane. The program calculates the height of the sample plane from the position of the objective. (In focusing devices which move the sample holder rather than the objective this step is dispensed with as the height of the sample plane does not change in this case.) Optionally, the program also requests the desired height of the introduction above the sample plane, if no value has been preset for this. The appropriate height of the pipette stop is calculated from this information, and the height is set accordingly. Setting the height of the pipette stop can also be extended to the transmitted-light illumination, with the result that both are moved simultaneously via a single system. It is thereby achieved that the focus of the transmitted-light illumination is likewise always appropriate to the focal plane.

A second variant of the invention provides coupling the illumination in annular manner, with the result that on the optical axis there remains an opening through which runs the pipette access channel. The annular illumination uses an illuminating, annular element which can be either an annular light source or an annular beam deflecting element. A condenser objective can be arranged between this illuminating element and the sample vessel in order to focus the illumination beam bundle. This condenser objective likewise has an opening on the optical axis through which opening runs the pipette access channel.

One possibility of the second variant for combining transmitted light and introduction of reagents consists of designing the transmitted-light source to be annular, with the result that a free passage is created along the optical ring. For this it is not important whether the illumination ring consists of individual point light sources or elements of the illuminated area. The diameter of the central opening needs to be large enough for the desired pipetting system or the tip of the pipette to fit through. In one embodiment, there are no optical elements between the light source and the sample plane. Thus, light made available from the source being concentrated on the sample field imaged by the objective does not happen. Instead of this, a high percentage of this light is lost as it is irradiated in divergent manner from the source. However, this loss can be overcome because a substantially higher number of individual light sources can be used in the ring illumination than is common in standard transmitted-light illuminations which possess only one spiral-wound filament or LED. In return, this illumination is very simple and consequently cost-favourable to achieve. The objective provides light from a NA (numerical aperture) region to the ring light, which aperture is determined by the diameter of the ring and the distance from the sample plane. The broader the surface being illuminated, the greater the usable NA region. Optionally, a diffusion disk is inserted between light source and sample in order to homogenize the light distribution and prevent the light structure from penetrating the image. This diffusion disk then likewise requires a central hole for the tip of the pipette.

In particular in multititer plates with a number of wells (e.g. 96 or 384), the wells themselves have a limiting effect on the illumination aperture. Therefore, it can happen that the light from the ring illuminations does not reach the bottom of the sample vessels because it is blocked by the edge of the well. Self-evidently, an annular light with a smaller diameter can be used a priori. However, the illumination then has only a very small numerical aperture, regardless of how many apertures the sample vessel permits. It is thus advantageous if the size of the annular light is matched to the type of sample vessel. Different annular lights can thus be used for different sample vessels. Alternatively, the height of the annular light can also be adjusted. Also, the angle at which the light radiates onto the sample can thereby be monitored. This height can be adjusted manually or using a motor.

Optionally, an objective with a central channel can be used (perforated customary lenses or annular-shaped Fresnel lenses). An increased complexity of the device helps achieve a better use of light. In order to use as much light as possible, the central channel should be as narrow as possible, which is why this device is occasionally incompatible with standard tips of pipettes. Then, a thin tube can be used which on the one hand guides the liquids to be pipetted through the objective and, on the other hand, protects the objective from the very same liquids. If the light is reflected along the introduction channel, the ring illumination including height adjustment can also be dispensed with and again a customary light source, such as a single LED, or a light filament can be transferred. The disadvantage then remains that a radial part of the illumination aperture is screened by the introduction channel. However, because the entire system can be designed such that the beam diameter is clearly bigger at the coupling point than directly over the sample, this screening has only a small influence on the illumination of the samples and is clearly less disruptive than if the tip of the pipette blocks the beam path laterally directly over the sample.

It is understood that the features mentioned above and those yet to be explained in the following are applicable, not only in the stated combinations, but also in other combinations or singly, without departure from the scope of the present invention.

BRIEF DESCRIPTION OF THE DRAWINGS

The invention is explained by way of example in yet greater detail in the following with reference to the attached drawings, which also disclose features essential to the invention. There are shown in:

FIGS. 1a-c are schematic representations of a first embodiment of a transmitted-light microscope;

FIG. 2 is a schematic representation of a second embodiment of a transmitted-light microscope;

FIG. 3 is a schematic representation of a third embodiment of a transmitted-light microscope;

FIG. 4 is a schematic representation of a fourth embodiment of a transmitted-light microscope;

FIG. 5 is a development of the transmitted-light microscope of FIGS. 1a-c;

FIG. 9 is a block diagram for a method for transmitted-light microscopy.

DETAILED DESCRIPTION OF THE DRAWINGS

Figure 6:
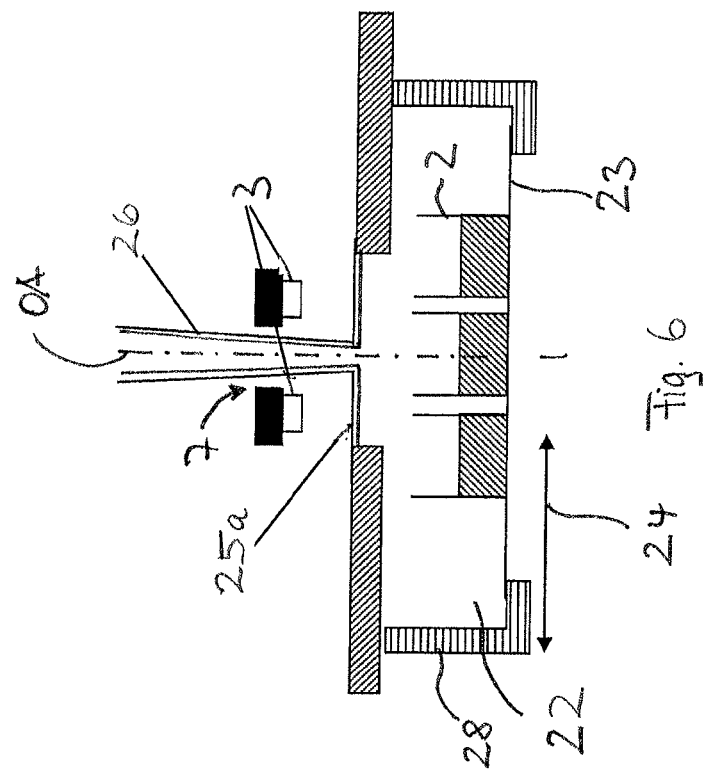
FIG. 6 is a view of an element of the microscope of FIG. 4.

FIGS. 1a-c show three different versions of a transmitted-light microscope 1 which is designed to subject a microtiter plate 2 to microscopy in transmitted light. The microscope 1 images individual wells 4 of the microtiter plate 2 in the transmitted light along an optical axis OA with an imaging beam path A. An annular light source 3 is provided for transmitted-light illumination, which light source illuminates from above the wells 4 of the microtiter plate 2 to be subjected to microscopy. The annular light source 3 is part of an illumination beam path B and irradiates radiation onto the well 4. The cone of light with which the bottom of the well 4 can be illuminated is numbered 5. Using a tip 6 of a pipette, a reagent is dropped into a liquid 8 located in the well 4. The tip 6 of the pipette is guided through a pipette access channel which is formed substantially by an opening 7 in the annular light source 3 which lies on the optical axis OA. The tip of the pipette can thereby be inserted along the optical axis OA and the reagent introduced, while simultaneously an objective 7 with camera 10 images the well 4 in an imaging beam path and e.g. also produces an enlarged image of the bottom of the well.

FIGS. b and 1c show an optional development of the microscope 1 of FIG. 1a to the extent that the height of the annular light 3 can be adjusted. The angle of the incident radiation is thus altered. Depending on the height of the annular light, a different part of the radiation enters the cone of light 5. A situation as in FIG. 1b is avoided, where the area determined by the opening 7 is so large that no light reaches the bottom of the well because of the aspect ratio of a well 4. By moving the annular light source 3 along the optical axis OA, it can be ensured that the light reaches the bottom of the well and thus the sample.

FIG. 2 shows a development of the microscope of FIG. 1a, wherein elements of the imaging beam path A are not drawn in for reasons of clarity. A condenser 11 is arranged between the annular light source 3 and the microtiter plate 2 in illumination beam path B, which condenser has a bore 12 appropriate to the opening 7. The opening 7 and the bore 12 thus form the pipette access channel though which can be pushed a tip of a pipette 7. Simultaneously, the condenser 11 homogenizes the illumination of the well 4 to be subjected to microscopy.

FIG. 3 shows a modification of the microscope 1 of FIG. 2 in which, instead of an annular light source 3, the illumination beam path B has a customary light source 13 with downstream objective 14 which illuminates a deflecting mirror 15 which couples the illumination beam along the optical axis OA. The illuminated deflecting mirror 15 thus assumes the function of the annular light source 3 as, like this, it has an opening 7 for clearing the pipette access channel.

Self-evidently, the deflecting mirror 15 can be used as a replacement for the annular light source 3 also in the design according to FIGS. 1a-c.

It is essential only that the illuminating element (for example the annular light source 3 or the deflecting mirror 15) has the opening 7 for the pipette access channel.

FIG. 4 shows a further embodiment of a transmitted-light microscope 1. The microscope 1 of FIG. 4 is likewise designed to subject a microtiter plate 2 to microscopy. Elements which correspond to those of the microscopes of FIGS. 1a-c, 2 or 3 are provided with the same reference numbers in FIG. 4.

The introduction of the reagent and the subjecting of the sample to microscopy takes place chronologically in the microscope 1 of FIG. 4. For this, the microscope 1 has a block 16 which has a chamber 17 for receiving the elements of the illumination beam path B and a through channel 18.

The chamber 17 has, at its lower end, a passage 19 through which illumination radiation can be emitted along the optical axis OA onto the well 4 of the microtiter plate 2 to be subjected to microscopy. For example, a light source for emitting the illumination radiation and a corresponding objective for conditioning the illumination radiation in the chamber 17 (for reasons of simplicity not drawn in FIG. 4) is located there.

FIG. 5 shows, schematically, a section through the block 16 along the line C-C. As can be seen, the block 16 can be rotated about an axis of rotation 20. This is the movement along the arrow 21. The rotational movement along the arrow 21 is a single movement which moves the block 16 between two end positions. FIG. 5 shows the first of these two end positions which lies such that the chamber 17 is aligned to the optical axis OA with the elements of the illumination beam path B. Understandably, the representation of FIG. 5 shows only one point of passage for the optical axis OA.

The rotation, i.e. the single movement along the arrow 21, can alternatively move the through channel 18 over the microtiter plate 2 and the well 4 to be subjected to microscopy there. Then, the second of the two end positions is reached in which the through channel 18 lies on the optical axis OA and the reagent can be introduced into the well 4 of the microtiter plate 2.

Naturally, the block 16 can also be modified. Thus, for example, instead of the chamber 17 closed at the top, in which the elements of the illumination beam path are accommodated, also an illumination channel can be provided in the block 16 and elements of the illumination beam path can be arranged over the block if a corresponding deflecting mirror is provided at the block 16 over the passage 19, which mirror only then receives radiation if the block 16 is moved into the position shown in FIG. 4 or 5.

A further modification consists of the single movement being not a rotational movement, but a linear movement. The block 16 is then moved between the two end positions.

Figure 7:
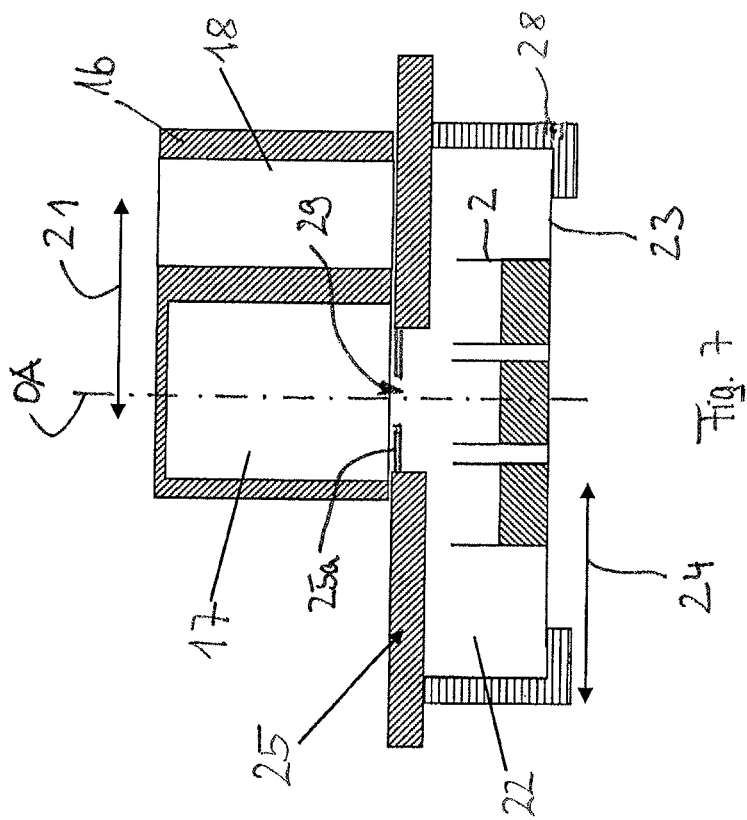
FIG. 7 is a development of the microscope of FIG. 4.

FIGS. 6 and 7 show modifications of the of FIGS. 1a-c or 4. They comprise an incubation chamber 22 as is known for example from DE 102005033927 A1 for a microscope reading out from microtiter plates. The incubation chamber 22 has a table 23 on which the microtiter plate 2 can be moved along the arrow 24. It is covered with a cap 25 and closed to the side by a lateral sample holder 28. The microtiter plate 2 is moved either by the table 23 in the incubation chamber or alternatively by moving the lateral receivers 28. The advantage of the latter solution is that the incubated space can be kept very small and thus only small gas volumes and short heating-up times are necessary.

The advantage of both designs lies in the fact that the complete transmitted-light illumination lies outside of the incubated space. Herein lies the difference from DE 102005033927 A1. As a result, e.g. all electrical elements can be kept outside of the area of increased temperature and atmospheric humidity of the incubation chamber 22.

The incubation chamber 22 can be used either with the annular illumination element, e.g. the annular light source according to FIGS. 1*a-c*, or also with the microscope according to FIG. 4, i.e. a chronological sequence of pipetting and microscopic imaging.

In the design of FIGS. 1*a-c* it is advantageous that the cover 25 is part of the microscope and has a transparent part 25*a* which ends in a pipette nozzle 26 which runs along the optical axis OA through the opening 7 of the annular light source (or of the deflecting mirror 15) and simplifies insertion of the tip of the pipette. The cover 25 can also be used for further sealing the incubated space also in the design of FIG. 7 (there it is, of course, optional). It then has a hole 29 through which the reagent can be introduced if the block 16 is in the second end position in which the through channel 18 is aligned to the optical axis OA.

Figure 8:
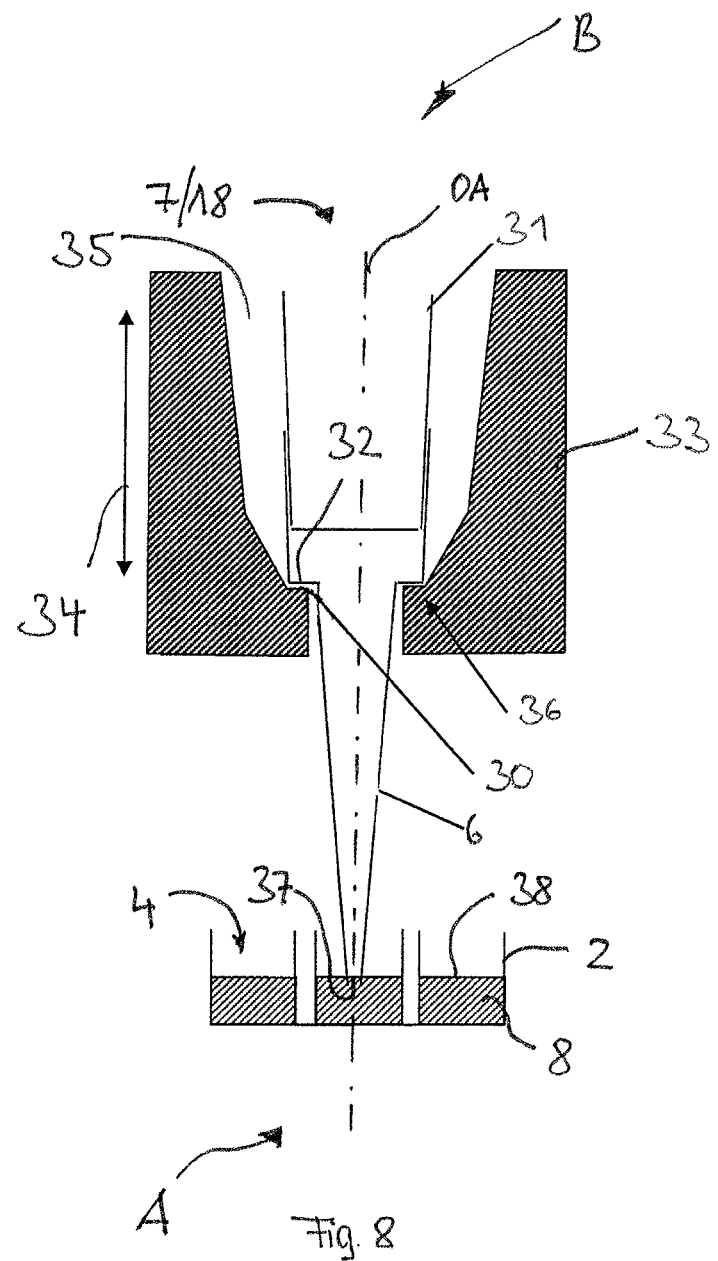
FIG. 8 is a representation of a pipette stop in the microscope of FIG. 4.

FIG. 8 shows an optional development in the form of a pipette holder 33 which can be used either in the designs of FIGS. 1*a-c*, 2 and 3 or also in the designs of FIGS. 4, 5 and 7. In the latter variant, the holder 33 lies in the through channel 18, in the former, in the opening 7. FIG. 8 illustrates this with the reference numbers 7/18. The holder 33 has a receiver 35 which tapers at its bottom end into a collar 30. The collar 30 serves as a stop 36 for a shoulder 32 provided at the tip 6 of the pipette. The holder 33 thus defines the exact position of the tip 6 of the pipette if a pipette 6 is pushed into the receiver 35.

As an arrow 34 illustrates, the holder 33 can be adjusted along the optical axis OA in order for adaptation to various lengths of the tip of the pipette, already mentioned in the general part of the description, to be carried out, and to ensure that the bottom end 37 of the tip 6 of the pipette lies below a liquid level 38 of the liquid 8 in the well 4 of the microtiter plate 2.

The invention relates likewise to a transmitted-light microscope and to a method for transmitted-light microscopy. The corresponding method steps are optionally carried out using a control apparatus C which is drawn in by way of example for the microscope of FIG. 4, but likewise can be provided for the other embodiments of the microscope.

The block 16 can be moved along the arrow 21 which symbolises the movement path, controlling the control apparatus C, wherein the block 16 is actuated by a drive mechanism (not shown).

FIG. 9 shows, schematically, a block diagram for a method for transmitted-light microscopy, wherein the holder 33 is used.

In a step S1, firstly a check is carried out as to which tip 6 of the pipette is used. With this information to hand, the distance between the shoulder 23 and the bottom end 27 of the tip 6 of the pipette is ascertained. This takes place in a step S2.

In a step S3 a check is carried out as to whether the desired sample plane lies in the focus of the objective 6. If this is the case ("+" intersection) the method skips to step S5. If this is not the case ("−" intersection), firstly the objective is brought into focus in a step S4.

In step S5, the focus position is read in and the height of the sample is ascertained. From this height of the sample, the height of the liquid level 28 is automatically known because of the further known type of sample. Now, knowing the distance between the bottom end 37 and the shoulder 32 as well as the liquid level 38, the intended height of the collar 30 and thus the holder 33 is calculated (S6). Alternatively, a height of the tip of the pipette above the sample plane, predetermined by the user, can also be used as a parameter. Then, the height of the liquid is no longer relevant.

Subsequently, in a step S7, the holder 33 is adjusted in the direction of the arrow 34, i.e. along the optical axis OA, such that, in respect of the liquid level 38, a pipette 31 inserted into the holder 33 with the tip 6 of the pipette, the values of which have been ascertained in steps S1 and S2, lies such that the bottom end 37 of the tip 6 of the pipette is immersed accurately into the liquid 8. Of course, step S7 can also be carried out manually in part. For this, the user is then given the information concerning the height at which he needs to position the stop in order to reach the desired pipetting height above the sample planes.

The invention claimed is:

1. A transmitted-light microscope for imaging sample vessels, the microscope comprising:
   an illumination beam path for illuminating a sample vessel from above with an illumination beam bundle along an optical axis;
   an imaging beam path for imaging the sample vessel from below along the optical axis;
   a pipette access channel for introducing a reagent into the sample vessel;
   a block having a passage for the illumination beam bundle, and a through channel, the pipette access channel extending through the through channel, wherein the through channel and the passage lie adjacent to one another in a plane perpendicular to the optical axis, the block being selectively positionable in a first position in which the through channel is aligned to the optical axis, and a second position in which the passage is aligned to the optical axis;
   a guide device for the block defining a path between the first position and the second position, wherein the block is shiftable along the path in a single movement; and
   a drive mechanism for driving movement of the block between the first position and the second position.

2. The transmitted-light microscope of claim 1, wherein the single movement is a rotational movement.

3. The transmitted-light microscope of claim 1, wherein the single movement is a linear movement along an axis.

4. The transmitted-light microscope of claim 3, wherein the axis is perpendicular to the optical axis.

5. The transmitted-light microscope of claim 1, wherein the through channel has an annular collar which functions as a stop for a tip of the pipette.

6. The transmitted-light microscope of claim 5, wherein the stop can be moved along the optical axis.

7. The transmitted-light microscope of claim 1, wherein a transparent cover is provided over the sample vessel, which cover has a hole on the optical axis, through which hole the reagent is introduced.

8. A method for transmitted-light microscopy of vessels, comprising:
   illuminating a sample vessel from above along an optical axis with an illumination beam bundle;
   imaging the sample vessel from below along the optical axis;

introducing a reagent into the sample vessel via a pipette access channel in a through channel in a selectively positionable block, wherein the block further has a passage for the illumination beam bundle adjacent to the through channel in a plane perpendicular to the optical axis; and positioning the block in a single movement between a first position in which the through channel is aligned with the optical axis, and a second position in which the passage is aligned with the optical axis.

9. The method according to claim 8, wherein a distance between a bottom end of the tip of a pipette in the pipette access channel, and a bottom, an edge or a liquid level of the sample vessel is ascertained from information about the tip of the pipette used, and the stop is set such that the bottom end of the tip of the pipette is in a predetermined position relative to the liquid level.

* * * * *

UNITED STATES PATENT AND TRADEMARK OFFICE
CERTIFICATE OF CORRECTION

PATENT NO.        : 9,594,241 B2
APPLICATION NO.   : 14/795530
DATED             : March 14, 2017
INVENTOR(S)       : Peter Schoen et al.

It is certified that error appears in the above-identified patent and that said Letters Patent is hereby corrected as shown below:

In the Specification

At Column 7, Line 42, please delete "FIGS. $b$ and $1c$ show an optional development of the microscope 1 of FIG. $1a$ to the extent that the height of the annular light 3 can be adjusted." and insert -- FIGS. $1b$ and $1c$ show an optional development of the microscope 1 of FIG. $1a$ to the extent that the height of the annular light 3 can be adjusted. --

Signed and Sealed this
Fourth Day of July, 2017

Joseph Matal
*Performing the Functions and Duties of the*
*Under Secretary of Commerce for Intellectual Property and*
*Director of the United States Patent and Trademark Office*